(12) United States Patent
Azimi et al.

(10) Patent No.: US 10,012,639 B1
(45) Date of Patent: Jul. 3, 2018

(54) GAS-SENSING APPARATUS WITH A SELF-POWERED MICROHEATER

(71) Applicants: Saeed Azimi, Los Gatos, CA (US); Elaheh Farjami, San Jose, CA (US)

(72) Inventors: Saeed Azimi, Los Gatos, CA (US); Elaheh Farjami, San Jose, CA (US)

(73) Assignee: DYNOSENSE, CORP., San Jose, CA (US)

(*) Notice: Subject to any disclaimer, the term of this patent is extended or adjusted under 35 U.S.C. 154(b) by 198 days.

(21) Appl. No.: 15/195,644

(22) Filed: Jun. 28, 2016

Related U.S. Application Data

(63) Continuation-in-part of application No. 15/178,407, filed on Jun. 9, 2016.

(51) Int. Cl.
*G01N 33/00* (2006.01)
*G01N 33/497* (2006.01)
*A61B 5/08* (2006.01)

(52) U.S. Cl.
CPC .......... *G01N 33/497* (2013.01); *A61B 5/082* (2013.01); *G01N 33/0031* (2013.01); *G01N 33/0036* (2013.01); *G01N 33/0054* (2013.01); *G01N 33/4972* (2013.01)

(58) Field of Classification Search
CPC ............. G01N 33/497; G01N 33/0031; G01N 33/0036; G01N 33/0054; G01N 33/4972
See application file for complete search history.

(56) References Cited

U.S. PATENT DOCUMENTS

2013/0344609 A1* 12/2013 Mayer .................. G01N 33/497
436/133

OTHER PUBLICATIONS

Article titled "Air-Activated Ration Heaters" by Paul DellaRocca published in Dec. 2008.*

* cited by examiner

*Primary Examiner* — Blake A Tankersley
(74) *Attorney, Agent, or Firm* — Plager Schack LLP

(57) ABSTRACT

A gas-sensing apparatus with a self-powered microheater to reduce power usage and enhance efficiency when determining a presence of one or more gases in an air sample is provided. The gas-sensing apparatus includes a substrate, a sensing layer coupled to the substrate, and a heater element connected to the sensing layer and having at least one sheet. The sheet is made from a homogenous mixture of zinc powder and activated carbon. Oxygen from ambient air interacts with zinc ions in the zinc powder in an exothermic reaction to generate heat energy for use in heating the sensing layer to a desired temperature, thereby permitting the sensing layer at the desired temperature to detect the presence or ratio of the one or more gases in the air sample.

7 Claims, 3 Drawing Sheets

GAS-SENSING APPARATUS WITH A SELF-POWERED MICROHEATER

RELATED APPLICATION

The application claims priority to non-provisional patent application U.S. Ser. No. 15/178,407 filed on Jun. 9, 2016, the entire contents of which is herein incorporated by reference.

BACKGROUND

The embodiments herein relate generally to devices for determining the gases present in an air sample or breath sample.

The human breath is complex and is estimated to have as many as 200 different gas components in a typical sample. Some of these gases are present in small quantities such as 1-100 parts per billion (ppb), which presents a need for accurate methods and devices to properly detect these components.

Several techniques available in the field such as chemoresistive analyses are used to determine the ratio of gases present in a sample. During these analyses, gases in a sample interact with sensors, which causes the resistance properties of the sensors to change. The sensing material of the chemo-sensors are generally heated to a high temperature within the range of 50-700 degrees Celsius. This heating process increases the selectivity and sensitivity of the chemo-sensors to the present gases at certain temperatures. By measuring the resistances of one or more chemo-sensors at various temperatures, the ratio of gases present in a sample can be estimated. Therefore, it is critical when performing chemo-resistive analyses to heat each sensor to a particular temperature by using a microheater element.

The development of microheaters (microhotplates) as platforms for microsensors has been widely reported for gas sensing applications. However, the cost and design of the microheaters is challenging, particularly for portable and disposable gas sensing applications. For example, the serpentine polysilicon heater or other conductive materials must be embedded within two electrically insulating members (e.g. $SiO_2$ layers) several micrometers in thickness. Further, fabricating a low power sensor with rapid heating or cooling characteristics with a surface that is easy to clean poses many challenges. Current microheaters have these limitations and require external power sources such as batteries or power outlets to operate. This limits the practicality of the devices and places several burdens on the operator.

As such, there is the need for a low power gas-sensing apparatus with reduced power requirements that addresses the limitations of the prior art, which includes a self-powered microheater.

SUMMARY

A gas-sensing apparatus with a self-powered microheater to reduce power usage and enhance efficiency when determining a presence of one or more gases in an air or breath sample is provided. The gas-sensing apparatus comprises a substrate, a sensing layer coupled to the substrate, and a heater element operably connected to the sensing layer and comprising at least one sheet, the sheet comprising a homogenous mixture of zinc powder and activated carbon, wherein oxygen from ambient air is configured to interact with zinc ions in the zinc powder in an exothermic reaction to generate heat energy for use in heating the sensing layer to a desired temperature, thereby permitting the sensing layer at the desired temperature to detect the presence or ratio of the one or more gases in the air or breath sample.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figure 1:
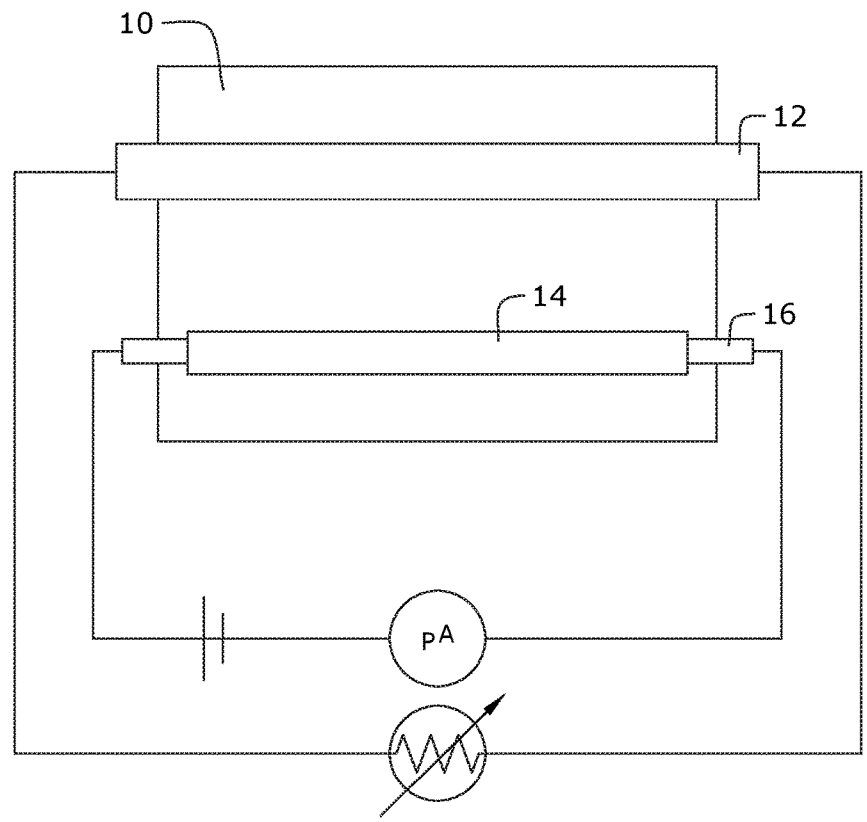
FIG. 1 depicts a schematic view of certain embodiments of the gas-sensing apparatus.

As depicted in FIG. 1, the gas-sensing apparatus comprises microheater 10, thermistor 12 and sensing layer 14, and is configured to determine a ratio and/or presence of gases in a breath sample or air sample. Microheater 10 is operably connected to both sensing layer 14 and thermistor 12 via a circuit. Sensing layer 14 may be coupled to thermistor 12 and/or microheater 10 by members such as metal contact 16.

In certain embodiments, sensing layer 14 is coupled to a substrate (not shown), which is preferably made from glass or other flexible polymer. In one embodiment, sensing layer 14 is coupled to the substrate by using an inkjet printing process. The substrate is also configured to house and/or support microheater 10. In certain embodiments, sensing layer 14 may be a sensor array that includes any number and type of materials including, but not limited to, semiconducting oxides such as $WO_3$, $MoO_3$, $SnO_2$, $TiO_2$ and $Sb:SnO_2$, polymers such as polyaniline and polypyrrole, and metal catalysts such as Pd, Pt, Ni, Cu, Ag and Fe. These exemplary sensing materials are used for determining the presence of certain compounds in an air or human breath sample such as acetone, ethanol, methanol, ammonia, carbon dioxide, nitric oxide, or the like.

Microheater 10 is a self-powered heater made from a homogeneous mixture of zinc powder and activated carbon that is embedded into an appropriate polymer based binder system such as natural and/or synthetic rubber, polysulfone, acrylic, polymer, epoxy resin, polystyrene, polyterafluoro, ethylene or water-based agar binders. The homogeneous mixture is rolled into sheets to form microheater 10. In an alternative embodiment, microheater 10 may be formed from stable ink that is created by mixing zinc powder nanoparticles, activated carbon and a polymeric binder. In this embodiment, the stable ink will be deposited directly on the substrate using an inkjet printing technique.

Figure 2:
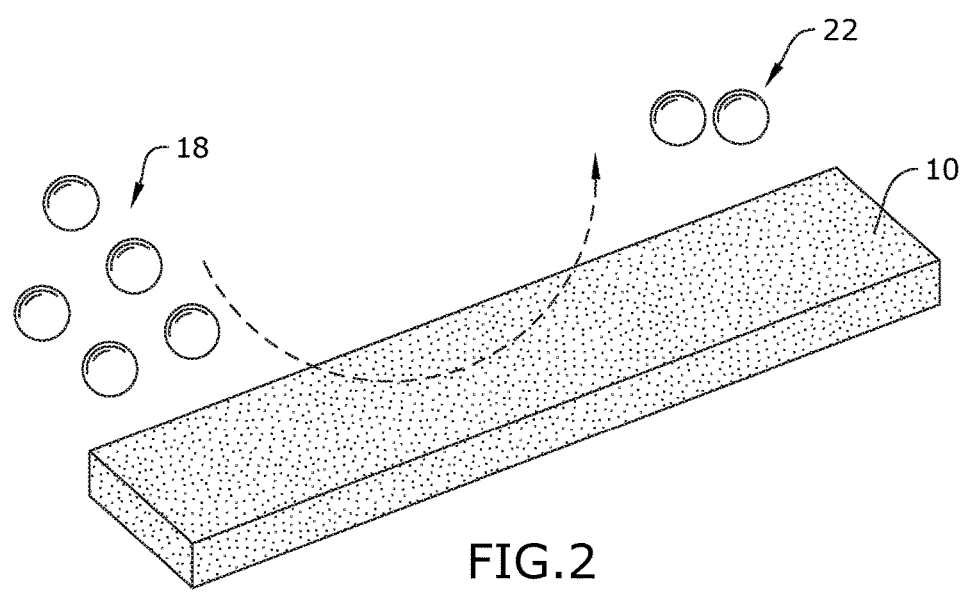
FIG. 2 depicts a schematic view of certain embodiments of the heat generation mechanism of the gas-sensing apparatus.

As depicted in FIG. 2, oxygen 18 from the ambient air interacts with zinc ions present in microheater 10 to produce output 22, which comprises zinc oxide and heat energy. This exothermic reaction is denoted by the following: $2\ Zn+O_2 \rightarrow 2\ ZnO$ wherein $\Delta H_f = -1.28$ kcal/g. The heat energy of output 22 is configured to heat sensing layer 14 to a desired temperature without the need for an external power source such as a power outlet, batteries, or the like. Activated carbon in the homogeneous mixture of microheater 10 comprises a porous structure, which improves oxygen circulation throughout the mixture to enhance heating characteristics of microheater 10. In addition, the activated carbon is a conductive element that permits a user (not shown) to measure conductivity changes of the element during the heating process.

The kinetics of the exothermic reaction can be adjusted by optimizing the thickness and composition thickness of the sheet in microheater 10 or the inkjet printed layer. By adjusting the reaction between zinc ions in microheater 10 and oxygen 18, a user can optimize the temperature range appropriate for gas sensing by sensing layer 14. Alternatively, the ratio of elements used, i.e., zinc oxide and activated carbon plus binders, can be varied to adjust the kinetics of the exothermic reaction as desired.

Thermistor 12 is coupled to microheater 10 by using an inkjet printing process and is preferably made from a semiconducting metal oxide like NiO, doped crystalline ceramic like BaTio3, or polymer such as Polyswitch. Thermistor 12, a resistor having a resistance dependent on the temperature, is configured to self-regulate microheater 10. This permits the temperature of sensing layer 14 to be adjusted appropriately for gas sensing applications. In certain embodiments, thermistor 12 may comprise an array of thermistors (not shown), which can be assembled in various configurations as desired.

In operation, the gas-sensing apparatus is assembled as depicted in FIG. 1. Microheater 10 is configured to generate heat energy when oxygen 18 from the ambient air interacts with zinc ions present in microheater 10. The generated heat energy heats sensing layer 14 to a desired temperature. This increases the selectivity and sensitivity of sensing layer 14 to certain gases at the desired temperature(s). In one embodiment, at least one resistance sensor (not shown) is coupled to sensing layer 14 to measure the resistance in the layer as it is heated by microheater 10. Since the resistance properties of sensing layer 14 at a particular temperature change in the presence of certain gases, the presence and/or ratio of gases present in an air or breath sample can be determined.

Figure 3:
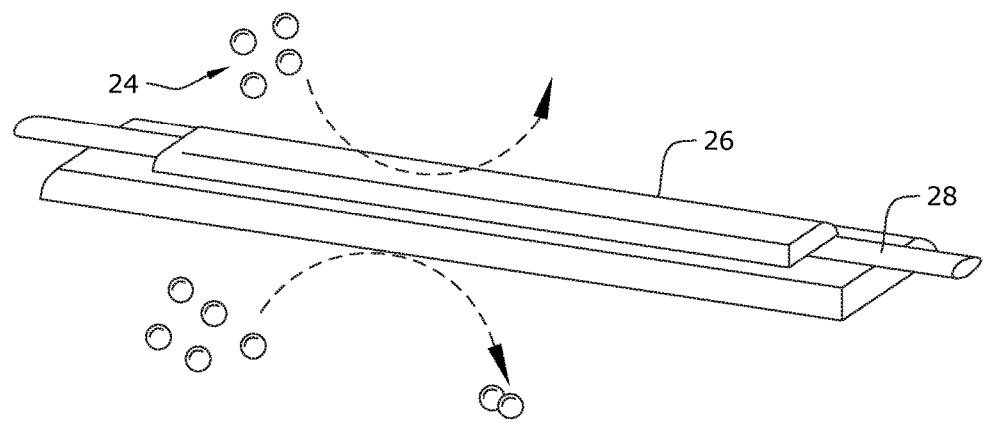
FIG. 3 depicts a schematic view of certain embodiments of the ammonia gas-sensing apparatus.
Figure 4:
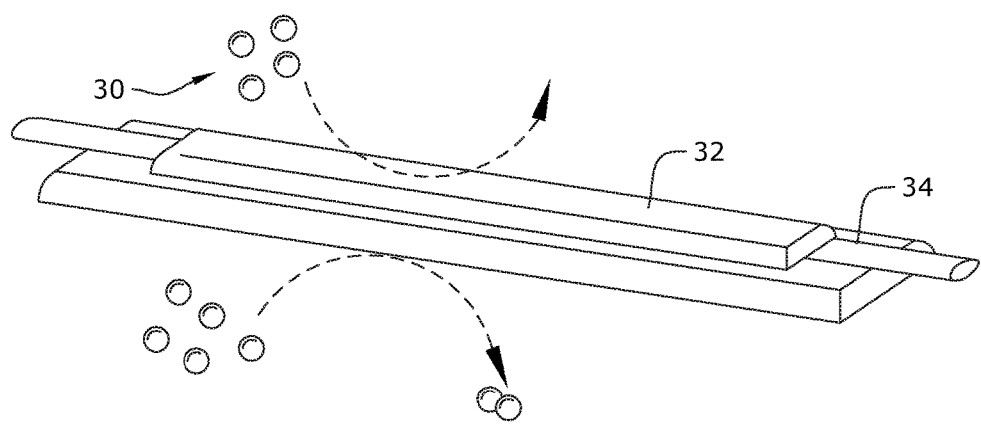
FIG. 4 depicts a schematic view of certain embodiments of the ethanol gas-sensing apparatus.
Figure 5:
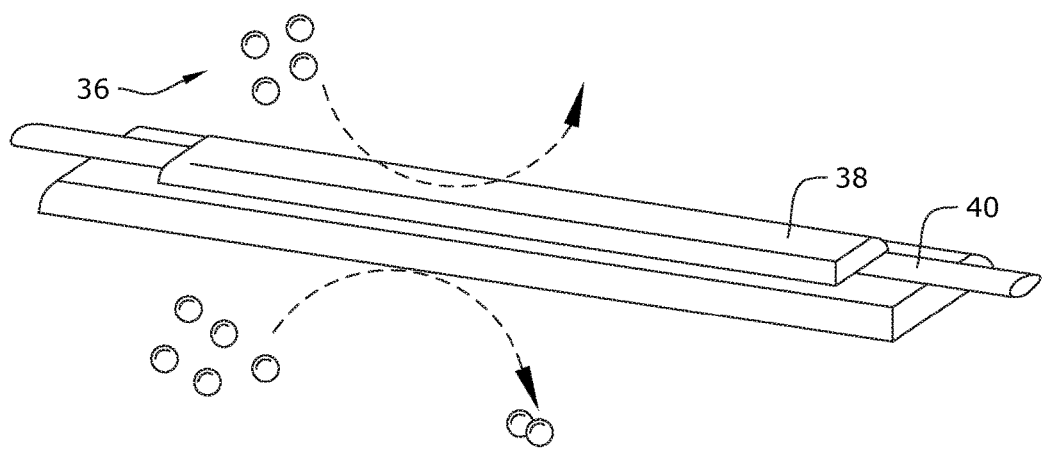
FIG. 5 depicts a schematic view of certain embodiments of the acetone gas-sensing apparatus.

FIGS. 3-5 illustrate alternative embodiments where sensing layer 14 is configured to detect different gases in an air or breath sample. FIG. 3 depicts a sensing layer comprising ammonia sensing layer 26 and ammonia sensing metal contact 28, which permits gas-sensing apparatus to detect ammonia 24 when ammonia sensing layer 26 is heated to a particular temperature. FIG. 4 depicts a sensing layer comprising ethanol sensing layer 32 and ethanol sensing metal contact 34, which permits gas-sensing apparatus to detect ethanol 30 when ethanol sensing layer 32 is heated to a particular temperature. FIG. 5 depicts a sensing layer comprising acetone sensing layer 38 and acetone sensing metal contact 40, which permits gas-sensing apparatus to detect acetone 36 when acetone sensing layer 38 is heated to a particular temperature. It shall be appreciated that ammonia sensing layer 26, ethanol sensing layer 32, acetone sensing layer 38 or other sensing layers may be combined together to form a sensor array to permit gas-sensing apparatus to detect the presence and/or ratio of multiple gases in an air or breath sample.

In certain embodiments, a computer processor (not shown) may be operably connected to sensing layer 14, thermistor 12 and the resistance sensor to record and/or analyze any operational data associated with the detection of gases in an air or breath sample. By analyzing the resistance changes of one or more gas sensing layers in sensing layer 14 at different temperatures, the presence and/or ratio of gases in an air sample can be determined.

It shall be appreciated that the components of the gas-sensing apparatus described in several embodiments herein may comprise any alternative known materials in the field and be of any color, size and/or dimensions. It shall be appreciated that the components of the gas-sensing apparatus described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A gas-sensing apparatus with a self-powered microheater to reduce power usage and enhance efficiency when determining a presence of one or more gases in an air sample, the gas-sensing apparatus comprising:
   a substrate;
   a sensing layer coupled to the substrate; and
   a heater element operably connected to the sensing layer and comprising at least one sheet, the sheet comprising a homogenous mixture of zinc powder and activated carbon, wherein oxygen from ambient air is configured to interact with zinc ions in the zinc powder in an exothermic reaction to generate heat energy for use in heating the sensing layer to a desired temperature, thereby permitting the sensing layer at the desired temperature to detect the presence or ratio of the one or more gases in the air sample.

2. The gas-sensing apparatus of claim 1, further comprising a thermistor operably connected to the heater element.

3. The gas-sensing apparatus of claim 2, wherein the thermistor is made from a material selected from the group consisting of a semiconducting metal oxide, doped crystalline ceramic and polymer.

4. The gas-sensing apparatus of claim 2, further comprising a resistance sensor operably connected to the sensing layer, wherein the resistance sensor is configured to measure resistance in the sensing layer.

5. The gas-sensing apparatus of claim 4, wherein the sensing layer comprises a sensor array, wherein the sensor array comprises an ammonia sensing layer.

6. The gas-sensing apparatus of claim 4, wherein the sensing layer comprises a sensor array, wherein the sensor array comprises an ethanol sensing layer.

7. The gas-sensing apparatus of claim 4, wherein the sensing layer comprises a sensor array, wherein the sensor array comprises an acetone sensing layer.

* * * * *